United States Patent
Shimizu et al.

(10) Patent No.: US 8,030,027 B2
(45) Date of Patent: Oct. 4, 2011

(54) METHOD FOR ENHANCING RECOMBINANT ANTIBODY PRODUCTION

(75) Inventors: Yuichiro Shimizu, Memphis, TN (US); Linda M. Hendershot, Memphis, TN (US)

(73) Assignee: St. Jude Children's Research Hospital, Memphis, TN (US)

( * ) Notice: Subject to any disclaimer, the term of this patent is extended or adjusted under 35 U.S.C. 154(b) by 213 days.

(21) Appl. No.: 12/424,116

(22) Filed: Apr. 15, 2009

(65) Prior Publication Data

US 2009/0269810 A1  Oct. 29, 2009

Related U.S. Application Data

(60) Provisional application No. 61/048,608, filed on Apr. 29, 2008.

(51) Int. Cl.
*C12P 21/06* (2006.01)
*C12P 21/04* (2006.01)
*C07K 16/00* (2006.01)

(52) U.S. Cl. ............ 435/69.1; 435/70.1; 530/387.1

(58) Field of Classification Search .......... None
See application file for complete search history.

(56) References Cited

OTHER PUBLICATIONS

Miller et al., Expression of *Borrelia burgdorferi* erp genes during infection of non-human primates, Microbial Pathogenesis, 2005, vol. 39, pp. 27-33.*
Meunier al., A Subset of Chaperones and Folding Enzymes Form Multiprotein Complexes in Endoplasmic Reticulum to Bind Nascent Proteins, Molecular Biology of the Cell, vol. 13, pp. 4456-4469.*
Shimizu et al., pERp1 is significantly up-regulated during plasma cell differentiation and contributes to the oxidative folding of immunoglobulin, PNAS, vol. 106, pp. 17013-17018.*
Anken et al., Efficient IgM assembly and secretion require the plasma cell induced endoplasmic reticulum protein pERp1, PNAS, vol. 106, pp. 17019-17024.*
Katoh et al., "*MGC29506* gene, frequently down-regulated in intestinal-type gastric cancer, encodes secreted-type protein with conserved cysteine residues", International Journal of Oncology 2003 23:235-241.

* cited by examiner

*Primary Examiner* — Alexander Kim
(74) *Attorney, Agent, or Firm* — Licata & Tyrrell P.C.

(57) ABSTRACT

The present invention is a method for enhancing recombinant antibody production by co-expressing in a host cell a recombinant antibody and ERp23 protein, which facilitates oxidative folding and stability of the recombinant antibody thereby enhancing production.

1 Claim, 1 Drawing Sheet

```
           (1)   1         10        20        30        40        50
m ERp23    (1) MRLPLP-LLLLLGCRAILGSAGDRVSLSASAHTLDDEEKYSAHMPAHLR C
h ERp23    (1) MRLSLPLLLLLLGAWAIPGGLGDRAPLTATAPQLDDEEMYSAHMPAHLR C
Consensus  (1) MRLXXPXLLLLLGXXAIXGXXGDRXXLSASAXXLDDEEXYSAHMPAHLR C

(51)  51        60        70        80        90       100
m ERp23    (50) DAC RAVAFQMGQRLAKAEAKSHTPDASGLQELSESTYTDVLDQTCSQNWQ
h ERp23    (51) DAC RAVAYQMWQNLAKAETKLHTSNSGGRRELSELVYTDVLDRSCSRNWQ
Consensus  (51) DAC RAVAFQMXQXLAKAEXKXHTXXAXGXXELSEXXYTDVLDXSCSXNWQ (101) 101       110       120       130       140       150
m ERp23   (100) SYGVHEVNQMKRLTGPGLSKGPEPRISVMISGGPWPNRLSKTCFHYLGEF
h ERp23   (101) DYGVREVDQVKRLTGPGLSEGPEPSISVMVTGGPWPTRLSRTCLHYLGEF
Consensus (101) XYGVXEVXQMKRLTGPGLSXGPEPXISVMISGGPWPXRLSKTCXHYLGEF (151) 151       160       170       180   **** 189
m ERp23   (150) GEDQIYEAYRQGQANLEALLCGGTHGPCSQEILAQREEL   SEQ ID NO:1
h ERp23   (151) GEDQIYEAHQQGRGALEALLCGGPQGACSEKVSATREEL   SEQ ID NO:2
Consensus (151) GEDQIYEAHXQGXAXLEALLCGGXXGXCSXXIXAXREEL   SEQ ID NO:3
```

US 8,030,027 B2

METHOD FOR ENHANCING RECOMBINANT ANTIBODY PRODUCTION

This application claims the benefit of U.S. Provisional Application No. 61/048,608, filed Apr. 29, 2008, which is herein incorporated by reference in its entirety.

INTRODUCTION

This invention was made with government support under Grant No. GM54068 awarded by the National Institutes of Health. The government has certain rights in the invention.

BACKGROUND OF THE INVENTION

Recombinant DNA techniques have rapidly developed and are particularly useful in the production of antibodies, in particular therapeutic antibodies. Systems for the expression of recombinant genes are well-known and include expression in mammalian cells, insect cells, fungal cells, bacterial cells and transgenic animals and plants. The choice of expression system is dependent on the features of the encoded protein, for example post-translational modifications. Other considerations include the time and, in particular, the cost involved in the production of the desired quantity of material of the required quality. These latter considerations are particularly important in the production of therapeutic antibodies of the quality required for regulatory approval and in the quantities needed for treatment of large numbers of patients.

SUMMARY OF THE INVENTION

The present invention is a method for enhancing recombinant antibody production by co-expressing in a host cell a recombinant antibody and ERp23 protein.

DETAILED DESCRIPTION OF THE INVENTION

Figure 1:
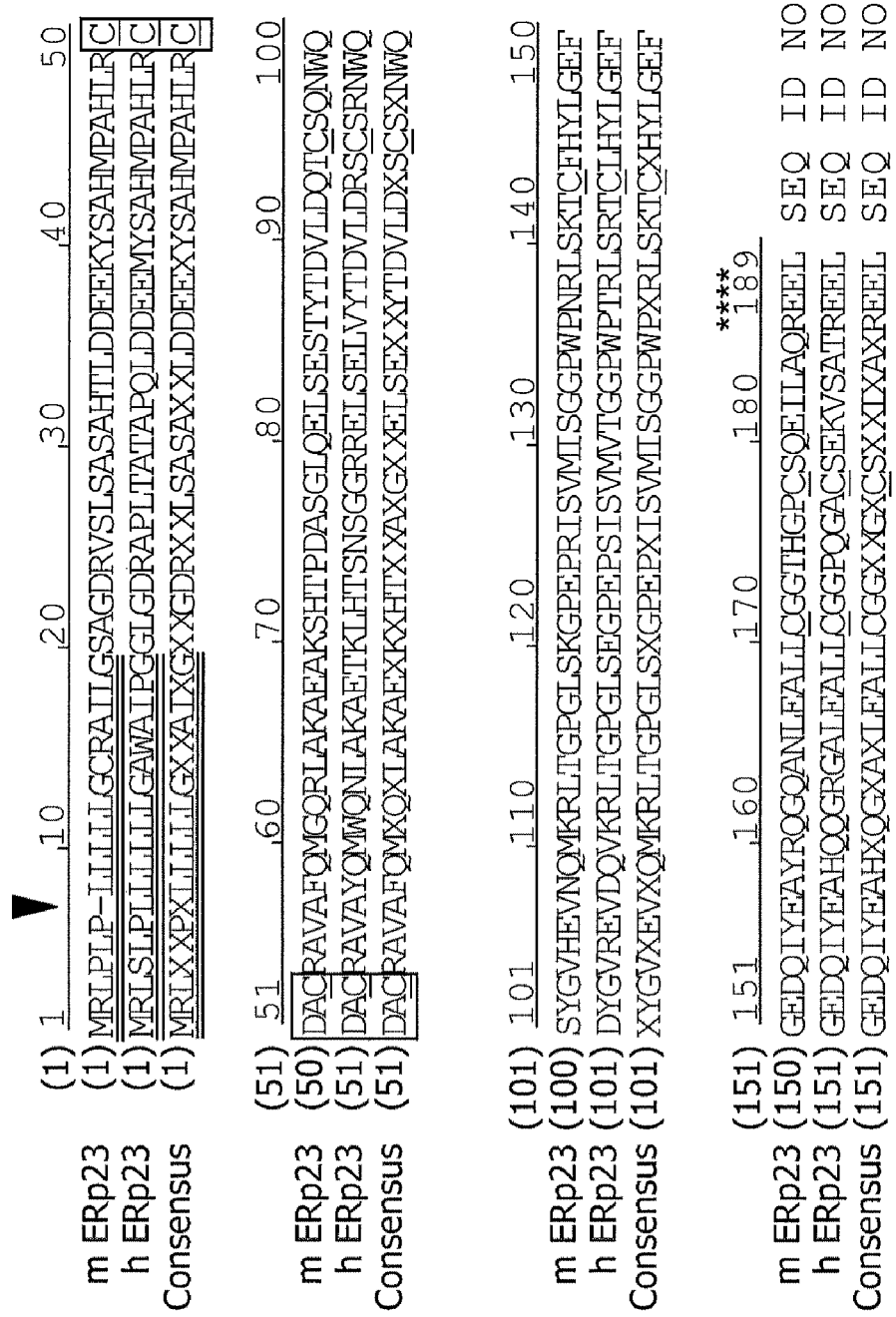
FIG. 1 depicts an amino acid sequence comparison between mouse ERp23 protein (SEQ ID NO:1) and human ERp23 protein (SEQ ID NO:2). The consensus sequence (SEQ ID NO:3) is shown as is a single amino acid insertion in the human sequence (arrow). The six conserved cysteine residues have a single underline, and the Cys-Xaa-Yaa-Cys (SEQ ID NO:4) motif is boxed. The predicted signal sequence is double underlined, and the endoplasmic reticulum retention signal is indicated with "*".

Plasma cells secrete vast quantities of immunoglobulin (Ig), which are heteromeric proteins composed of heavy chains (H) and light chains (L) that are folded and assembled in the endoplasmic reticulum (ER). Given that a single plasma cell can synthesize and secrete thousands of IgM pentamers, $(H_2L_2)_5$, per second, which requires the formation of ~100,000 disulfide bonds, plasma cells likely have particularly high demands on ER oxidoreductases. A novel lymphocyte-specific oxidoreductase (ERp23) has now been discovered that is a component of the BiP-Ig HC complex and is dramatically up-regulated during B-to-plasma cell differentiation. Although ERp23 has one thioredoxin-like active site motif (Cys-Xaa-Yaa-Cys; SEQ ID NO:4), it is largely α-helical nature indicates that it is unlikely to form the thioredoxin fold that contains the active site in most oxidoreductases, and ERp23 shares little homology with either Ero1 or Erv2, which are also α-helix-rich proteins that transfer disulfide bonds. Nonetheless, recombinant ERp23 was capable of refolding reduced/denatured Fab fragments as well as scrambled RNaseA in vitro. In addition, mixed disulfides between ERp23 and assembling IgM molecules were detected in differentiating B cells, indicating that ERp23 is an oxidoreductase and that Ig is the natural substrate of ERp23. Indeed, ERp23 was found to specifically oxidize the $C_H1$ domain of Ig heavy chains in an overexpression system, whereas diminishing the expression of ERp23 in lymphoid cells inhibited $C_H1$ domain oxidation. Unexpectedly, analysis of various cysteine mutants revealed that the initial cysteine in the Cys-Xaa-Yaa-Cys (SEQ ID NO:4) motif was not essential for the activity in vivo.

Accordingly, the present invention is based on the surprising and unexpected find that ERp23 represents a novel type of oxidoreductase which facilitates the oxidative folding and stability of recombinant antibodies thereby enhancing production of the same. This enables hugely beneficial savings in time and cost of production of quantities of functional antibodies of therapeutic quality.

Accordingly, the present invention is a method for enhancing the production of recombinant antibody molecules by co-expressing (i.e. concurrently expressing) in a host cell a recombinant antibody and ERp23 protein. In one embodiment, the recombinant antibody molecule includes at least part of an antibody heavy chain. In certain embodiments, the recombinant antibody molecule includes at least the $C_H1$ domain. In another embodiment, the recombinant antibody includes at least part of an antibody light chain. In this regard, the term "antibody" embraces full-length antibodies (i.e., containing both full-length heavy and light chains) and functionally active fragments, derivatives or analogues including, but not limited to, polyclonal, monoclonal, bi-, tri- or tetravalent antibodies, humanized or chimeric antibodies, single chain antibodies, such as Fab fragments, Fab' and Fab'$_2$ fragments, anti-idiotypic (anti-Id) antibodies, and epitope-binding fragments of any of the above. These antibodies and their fragments may be naturally occurring, humanized, chimeric or CDR grafted antibodies and standard molecular biology techniques may be used to modify, add or delete amino acids or domains as desired. Humanized antibodies are antibody molecules from non-human species having one or more complementarity determining regions (CDRs) from the non-human species and a framework region from a human immunoglobulin molecule (see, for example, U.S. Pat. No. 5,585,089). The antibody molecules produced by the method of this invention can be of any class (e.g., IgG, IgE, IgM, IgD and IgA) or subclass of immunoglobulin molecule.

As used herein, a recombinant antibody is intended to mean an antibody or antibody fragment produced by recombinant DNA technology. In particular embodiments, the recombinant antibody is a functional antibody. A recombinant antibody is said to be functional in that it retains the ability to specifically recognize or bind to the antigen against which it was raised (i.e., cognate antigen). The production of a functional antibody is shown by the presence of a single band on non-reducing SDS-PAGE corresponding to the expected molecular weight of the antibody, or by a direct binding assay using BIACORE or other methods known to the person skilled in the art including, but not limited to, ELISA, western blot analysis and the like. Non-functional antibodies include fragments which do not recognize their cognate antigen, and include incorrectly-folded or incorrectly-assembled antibodies, free heavy and light chains, and fragments thereof, including partially degraded fragments of antibodies which do not recognize or bind to their cognate antigen.

Methods for creating recombinant antibody molecules are well-known and routinely practiced in the art and any suitable method can be employed herein to co-express a recombinant antibody and ERp23 protein. See, for example, WO 92/02551; Ward, et al. (1989) *Nature* 341:544; Orlandi, et al. (1989) *Proc. Natl. Acad. Sci. USA* 86:3833; Riechmann, et al. (1988) *Nature* 322:323; Bird, et al. (1988) *Science* 242:423; U.S. Pat. No. 5,585,089; WO 91/09967; Mountain & Adair (1992) *Biotechnol. Genet. Eng. Rev.* 10:1-142; Verma, et al. (1998) *J. Immunol. Meth.* 216:165-181); and U.S. Pat. No. 6,441,147.

Typically, antibody sequences are generated or amplified using single lymphocyte antibody methods based on the molecular cloning and expression of immunoglobulin variable region cDNAs generated from single lymphocytes that are selected for the production of specific antibodies. See, e.g., Babcook, et al. (1996) *Proc. Natl. Acad. Sci. USA* 93 (15):7843-7848 and WO 92/02551. Such methods rely on the isolation of individual antibody producing cells which are then clonally expanded and screened for those clones which produce an antibody which recognizes its cognate antigen. Subsequently, at least a portion of the nucleotide sequence encoding the antibody is isolated or amplified and cloned into a recombinant protein expression system for expression in a suitable host cell.

To achieve co-expression of the recombinant antibody and ERp23 protein, nucleic acid sequences encoding ERp23 protein are likewise isolated or amplified and cloned into a recombinant protein expression system for expression in the same host cell expressing the recombinant antibody of interest. In some embodiments, the recombinant antibody and ERp23 protein are cloned into and expressed from the same plasmid or vector. In other embodiments, the recombinant antibody and ERp23 protein are cloned into and expressed from a different plasmid or vector. Alternatively, the host cell the nucleic acid molecules encoding the recombinant antibody and ERp23 protein can be integrated into the host cell genome. Moreover, it is contemplated that the expression of the recombinant antibody and ERp23 protein can be from the same promoter or regulated independently of each other using different promoters, e.g., the ERp23 protein can be constitutively expressed and the recombinant antibody can be expressed from an inducible promoter (e.g., an IPTG inducible promoter).

ERp23 proteins which can be expressed in accordance with the present invention include mammalian ERp23 proteins including, but not limited to, human, mouse, rat, horse, dog, cat, and the like. In particular embodiments, the mammalian ERp23 protein is human. Exemplary ERp23 proteins are depicted in FIG. 1 and set forth in SEQ ID NO:1, SEQ ID NO:2, and SEQ ID NO:3.

In the method of the invention, a host cell can be a fermented cell or cell culture including, but not limited to, a bacterium (e.g., a gram-positive or gram-negative bacterium such as *E. coli*), a yeast (e.g., *Saccharomyces cerevisiae* or *Pichia pastoris*), a filamentous fungus (e.g., *Neurospora crassa*), a mammalian cell (e.g., CHO or hybridoma cells such as NSO cells), an insect cell (e.g., *Spodoptera frugiperda* such as SF9) or a plant cell (*Arabidopsis thaliana*). Desirably, the recombinant antibody and ERp23 protein are co-expressed in bacteria, e.g., *E. coli* (see, Verma, et al. (1988) supra; Simmons, et al. (2002) *J. Immunol. Methods* 263:133-147).

*E. coli* host cells can be naturally occurring *E. coli* strains or mutated strains capable of producing recombinant proteins. Examples of specific host *E. coli* strains include MC4100, TG1, TG2, DHB4, DH5α, DH1, BL21, K12, XL1BLUE and JM109. Examples also include modified *E. coli* strains, for example metabolic mutants and protease-deficient strains. An exemplary *E. coli* host is *E. coli* W3110 (ATCC 27,325) a commonly used host strain for recombinant protein fermentations. The recombinant antibody produced using the method of the present invention is typically transported to either the periplasm of the *E. coli* host cell or to the host cell culture supernatant, depending on the nature of the antibody and the scale of production. The methods for targeting proteins to these compartments are well-known in the art, for a review see Makrides (1996) *Microbiol. Rev.* 60:512-538. Examples of suitable signal sequences to direct proteins to the periplasm of *E. coli* include the *E. coli* PhoA, OmpA, OmpT, LamB and OmpF signal sequences. Proteins can be targeted to the supernatant by relying on the natural secretory pathways or by the induction of limited leakage of the outer membrane to cause protein secretion examples of which are the use of the pelB leader, the protein A leader, the co-expression of bacteriocin release protein, the mitomycin-induced bacteriocin release protein along with the addition of glycine to the culture medium and the coexpression of the kil gene for membrane permeabilization.

Expression of recombinant protein in the *E. coli* host cells can also be under the control of an inducible system, whereby the expression of the recombinant protein in *E. coli* is under the control of an inducible promoter. Many inducible promoters suitable for use in *E. coli* are well-known in the art and depending on the promoter, expression of the recombinant protein can be induced by varying factors such as temperature or the concentration of a particular substance in the growth medium (Baneyx (1999) *Curr. Opin. Biotechnol.* (1999) 10:411-421; Goldstein & Doi (1995) *Biotechnol. Annu. Rev.* 105-128). Examples of inducible promoters include the *E. coli* lac, tac, and trc promoters which are inducible with lactose or the non-hydrolyzable lactose analog, isopropyl-β-D-1-thiogalactopyranoside (IPTG) and the phoA, trp and araBAD promoters which are induced by phosphate, tryptophan and L-arabinose, respectively. Expression can be induced by, for example, the addition of an inducer or a change in temperature where induction is temperature-dependent. Where induction of recombinant protein expression is achieved by the addition of an inducer to the culture the inducer can be added by any suitable method depending on the fermentation system and the inducer, for example, by single or multiple additions or by a gradual addition of inducer through a feed. It will be appreciated that there may be a delay between the addition of the inducer and the actual induction of protein expression, for example, where the inducer is lactose there may be a delay before induction of protein expression due to utilization of pre-existing carbon sources.

*E. coli* host cell cultures (fermentations) can be cultured in any medium that will support the growth of *E. coli* and expression of the recombinant proteins. The medium can be any chemically defined medium, such as those provided in Pirt (1975) *Principles of Microbe and Cell Cultivation*, Blackwell Scientific Publications, with modifications where appropriate to control growth rate. An example of a suitable medium is SM6E as described by Humphreys, et al. (2002) *Prot. Exp. Purific.* 26:309-320.

Culturing of *E. coli* host cells can take place in any suitable container such as a shake flask or a fermentor/bioreactor depending on the scale of production required. Various large scale fermentors are available with a capacity of greater than 1,000 liters up to about 100,000 liters, wherein fermentation of *E. coli* can be performed in any suitable system, for example continuous, batch or fed-batch mode (Thiry & Cingolani (2002) *Trends Biotechnol.* 20:103-105) depending on the protein and the yields required.

While expression systems and culture conditions for *E. coli* are disclosed herein for illustrative purposes, the present invention is not limited to recombinant antibody production in *E. coli*. Indeed, recombinant antibodies are routinely produced using a variety of recombinant expression systems, host cells and culturing methods well-known to the skilled artisan. Recombinant antibody production using these alternative systems is expressed embraced by the present invention.

Subsequent to culturing or growth, the host cell is typically subjected to collection, e.g., from the fermentation medium by methods such as centrifugation, filtration or by concentration. In this regard, the recombinant antibody can be isolated from the host cell or culture medium, depending on whether it is cytoplasmic or secreted. Recombinant antibody production can also include downstream purification procedures such as ion exchange chromatography, microfiltration, ultrafiltration, diafiltration, and fixed bed capture and expanded bed capture, or combinations of any of these. In this regard, the method of the invention is suitable for the large-scale industrial manufacture of antibodies of therapeutic quality, wherein co-expression of ERp23 protein with the recombinant antibody will facilitate the oxidative folding and stability of the recombinant antibody thereby enhancing production of the same when compared to production of the same recombinant antibody in the absence of ERp23 protein co-expression.

Antibodies prepared using the method of the invention are most desirably humanized antibodies, which can be linked to toxins, drugs, cytotoxic compounds, or polymers or other compounds which prolong the half-life of the antibody when administered to a patient.

The invention is described in greater detail by the following non-limiting examples.

EXAMPLE 1

Materials and Methods

Cell Lines and Antibodies. Mouse plasmacytoma cell line Ag8(8) ($\gamma^+$, $\kappa^-$) (Bole, et al. (1986) *J. Cell Biol.* 102:1558-66) were grown in complete RPMI-1640 medium containing 10% fetal bovine serum (FBS), 2 mM L-glutamine, 100 U/ml penicillin-streptomycin, and 55 µM 2-mercaptoethanol (2ME). 293T cells were cultured in DMEM supplemented with 10% FBS, 2 mM L-glutamine, and 100 U/ml penicillin-streptomycin. All cell lines were cultured at 37° C. under 5% $CO_2$.

The anti-ERp23 antibody was raised against recombinant human ERp23 (residues 75-190) fused to the amino-terminal glutathione S-transferase-tag (GST-ERp23) and expressed in *E. coli*. The antiserum from an immunized rabbit was subjected to ammonium sulfate precipitation (50% saturation), followed by absorption of antiserum first with recombinant GST protein bound to glutathione SEPHAROSE 4 fast flow (Amersham, Piscataway, N.J.), and subsequent affinity purification with amino-terminal His-tagged human ERp23 (residues 17-190) covalently coupled to CNBr-activated SEPHAROSE 4 fast flow (Amersham). Monoclonal anti-HA (12CA5) antibody is known in the art and commercially available from BAbCO, Richmond, Calif.), and monoclonal anti-PDI (M5/3H1) antibodies were from the Nara Inst. Sci. Tech. (Japan). Anti-mouse IgM (Igµ, κ and λ) were purchased from Southern Biotech (Birmingham, Ala.), and anti-actin from Santa Cruz Biotechnology, Inc. (Santa Cruz, Calif.).

Preparation of Cell Extracts, Transfection of Expression vectors, and Immunoprecipitation. Cells were lysed either by boiling in the presence of sodium dodecyl sulfate (SDS), or by buffer containing NONIDET P-40 (NP-40). For the SDS boiling method, cells were collected, rinsed with PBS and suspended in SDS lysis buffer (50 mM Tris-HCl (pH8.0), 0.6% SDS, 0.25 mM phenylmethylsulphonyl fluoride (PMSF), and protease inhibitor cocktail (Complete, Roche Diagnostics, Indianapolis, Ind.)). After incubation for 10 minutes at 95° C., samples were diluted with a 4-fold volume of buffer containing 10 mM sodium phosphate (pH 7.2), 2 mM EDTA, 0.25 M NaCl, 0.1% NP-40, 0.25 mM PMSF, and protease inhibitor cocktail, followed by centrifugation to remove debris.

For NP-40 extraction method, cells were collected, rinsed with PBS and suspended in NP-40 lysis buffer (50 mM Tris-HCl (pH 7.5), 0.15 M NaCl, 1% NP-40, 0.5% deoxycholic acid, 1 mM EDTA, 10% glycerol, 0.25 mM PMSF, and protease inhibitor cocktail). Proteins were extracted on ice for one hour and debris was removed by centrifugation.

Recombinant plasmids were introduced into cells by calcium phosphate precipitation according to conventional methods (Sambrook & Russell (2001) *Molecular cloning, third edition*, Cold Spring Harbor Laboratory Press).

For immunoprecipitation, antibodies were mixed with the cell lysate, and immune complexes were recovered by using protein A-SEPHAROSE (Sigma, St. Louis, Mo.). Since mouse Igγ expressed in Ag8(8) cells directly binds to the protein A, no antibodies were used for precipitating Igγ.

Isolation of Total RNA and Northern Analysis. Total RNA was isolated from cells using an RNEASY mini kit (QIAGEN, Valencia, Calif.). Northern blot analysis was performed by a standard method (Sambrook & Russell (2001) supra). DNA probes specific for human and mouse ERp23 and mouse 28S ribosomal RNA were amplified by RT-PCR using the following primer pairs; 5'-CTA CAC TTG CTG AAC TGG CTC CTG G-3' (SEQ ID NO:5) and 5'-GGA GGG TAG AGT CCA GGA CTA GAG CTC-3' (SEQ ID NO:6) for human ERp23, 5'-GCC ATG AGA CTG CCT CTG CCA C-3' (SEQ ID NO:7) and 5'-AAG CTC TTC TCT CTG GGC CAG G-3' (SEQ ID NO:8) for mouse ERp23, 5'-CTC AGT ACG AGA GGA ACC GC-3' (SEQ ID NO:9) and 5'-CGG ATT CTG ACT TAG AGG CG-3' (SEQ ID NO:10) for 28S ribosomal RNA. Probes were radiolabeled by using PRIME-IT II Random Primer Labeling Kit (Stratagene, La Jolla, Calif.) following the manufacturer's instructions.

Isolation of Primary B Cells and Induction of Plasma Cell Differentiation. Mouse B cells were enriched from spleen cells of 8-to-10 weeks old female C57BL/6 mice by depleting non-B cells with surface markers (CD3, CD4, CD8, Mac1, GR1 and TER119) using AUTOMACS (Miltenyi Biotec, Auburn, Calif.). Plasma cell differentiation was induced from splenic B cells by adding 50 µg/ml LPS (Sigma) to complete RPMI-1640 medium supplemented with 20% FBS, 2 mM L-glutamine, 100 U/ml penicillin-streptomycin, 55 µM 2ME, and 1× non-essential amino acids (Gibco-BRL, Grand Island, N.Y.) for up to four days.

Detection of Mixed Disulfides. Cells were washed with ice-cold PBS including 10 mM NEM for 5 minutes. Whole cells were directly lysed with pH 6.0 lysis buffer (40 mM sodium phosphate (pH 6.0), 150 mM NaCl, 1% NP-40, 0.1% SDS, 10% glycerol, 0.25 mM PMSF, and protease inhibitor cocktail), or precipitated under acidic conditions using 10% TCA to freeze all the post-lysis disulfide bond formation/reduction, followed by rinsing the pellet with 70% acetone twice, and re-dissolving the proteins in pH 6.0 lysis buffer.

Immunoprecipitated samples from the lysate were subjected to two-dimensional SDS-PAGE under non-reducing (first dimension), then reducing conditions (second dimension). After first dimension, the non-reducing gel lane was cut and incubated in 2× reducing SDS sample buffer at 50° C. for 20 minutes. The gel slice was rotated 90° and then applied to another SDS-PAGE gel for the second dimension electrophoresis. Spots were visualized either by autoradiography, if $^{35}$S was used, or by immunoblot analysis.

Metabolic Labeling and Pulse-Chase Experiments. For metabolic labeling (pulse), cells were incubated in methionine- and cysteine-free DMEM or RPMI1640 labeling medium containing 10% dialyzed FBS with $^{35}$S-TransLabel (MP Biomedicals, Irvine, Calif.) for indicated times. If necessary, the chase was initiated by washing the cells twice with cold PBS and then adding an excess of unlabeled methionine (2 mM) and cysteine (2 mM) to the chase media. Aliquots of cells were removed at the indicated times of chase, and cells were separated from the media and washed once with ice-cold PBS containing 10 mM NEM before lysing. The cell lysates were immunoprecipitated as indicated. In order to monitor the folding of the mini-HC, intensity of each form of bands were measured using a PHOSPHORIMAGER, and the percentage of the fully oxidized form was calculated. Mean values and standard errors are calculated from at least three independent experiments.

Purification of Recombinant Protein and In Vitro Assay. A cDNA construct of wild-type ERp23 that lacked the endoplasmic reticulum targeting signal sequence (residues 17-189) but encoded a hexa-histidine tag at its N-terminus was inserted into the pQE30 vector (QIAGEN) and expressed in *E. coli* strain M15. Recombinant proteins were purified using Nickel-NTA agarose (QIAGEN) and size exclusion chromatography 75 (SEC75; GE Healthcare, Piscataway, N.J.). The purity of the recombinant protein was ~98%.

Refolding of a denatured and reduced Ig Fab fragment was carried out according to conventional methods (Lilie, et al. (1994) supra). Purified recombinant ERp23 and PDI were reduced with 3 mM DTT before addition to the folding reaction. Scrambled RNase A assay was carried out using known methods (Walker, et al. (1996) supra). Briefly, renaturation of scrambled RNase A was monitored continuously by monitoring the hydrolysis of the RNase substrate, cCMP, at 296 nm, using a spectrophotometer.

EXAMPLE 2

Oxidoreductase Activity of ERp23

Mass spectrophometric analysis of a multi-chaperone complex associated with the unoxidized $C_H1$ domain of unassembled Ig heavy chains (Meunier, et al. (2002) *Mol. Biol. Cell* 13:4456-69) revealed the presence of ERp23 protein co-migrating at ~23 kDa with cyclophilin B and SPF-2. ERp23 was previously identified in a microarray study of gastric tumors, and alignment of ERp23 amino acid sequences from various species (Katoh & Katoh (2003) *Int. J. Oncol.* 23:235-41) identified six well-conserved cysteine residues including a single thioredoxin-like active site motif (Cys-Xaa-Yaa-Cys; SEQ ID NO:4) (indicated in box, FIG. 1), which is a hallmark of the oxidoreductases (Ellgaard & Ruddock (2005) *EMBO Rep.* 6:28-32). ERp23 also has an N-terminal signal sequence and an endoplasmic reticulum (ER) retention signal on its C-terminus, indicating that it is a soluble resident ER protein. In spite of its discovery in a gastric tumor, ERp23 expression appears to be lymphoid specific, since ERp23 transcripts were found to be most abundant in lymphoid tissues, such as thymus and spleen, with lesser amounts present in small intestine, which probably reflects the presence of gut-associated lymphoid tissues including Peyer's patches and abundant plasma cells. In fact, nearly all of the recorded ERp23 ESTs have been derived from lymphoid cells.

Since ERp23 was identified in a plasmacytoma cell line, the expression of ERp23 was determined during B-to-plasma cell differentiation using mouse primary cells. When normal splenic B cells were treated with the B cell mitogen lipopolysaccharide (LPS) to induce plasma cell differentiation, ERp23 protein and mRNA levels increased dramatically in concert with the up-regulation of the secreted form of Ig μ heavy chain. Protein Disulfide Isomerase (PDI), a well-characterized ubiquitously expressed oxidoreductase was also up-regulated during LPS-induced plasma cell differentiation (van Anken, et al. (2003) *Immunity* 18:243-53; Paver, et al. (1989) *FEBS Lett.* 242:357-62), albeit not as dramatically as ERp23. These results indicated ERp23 was involved in the synthesis of large amounts of Igs in plasma cells.

Although ERp23 has the canonical Cys-Xaa-Yaa-Cys (SEQ ID NO:4) motif associated with oxidoreductases, secondary structure predictions indicated that ERp23 was mostly α-helical with one possible β-sheet, such that it was very unlikely that ERp23 formed a thioredoxin-like fold, which is composed of five β strand sheets surrounded by four α-helices (Freedman, et al. (2002) *EMBO Rep.* 3:136-40). Circular dichroism spectra analysis of recombinant ERp23 indicated that indeed it was a largely α-helical protein. Two other predominantly α-helical flavoproteins, Ero1p and Erv2, have been identified that directly transfer disulfide bonds to PDI-like proteins (Tu & Weissman (2004) *J. Cell Biol.* 164:341-6). ERp23 shows no homology at the amino acid level with either of these proteins, but in the absence of a crystal structure for ERp23 it is not possible to determine if it forms a similar structure. Nonetheless, it was evaluated whether ERp23 possessed oxidoreductase activity.

First, it was determined whether ERp23 had oxidoreductase activity in vitro. Recombinant ERp23 was expressed in bacteria and purified to near homogeneity. The purified protein was directly tested for the ability to refold and assemble a denatured and reduced Ig Fab fragment in vitro (Lilie, et al. (1994) *J. Biol. Chem.* 269:14290-6). The results of this analysis indicated that while PDI refolded the Fab fragment up to ~18%, ERp23 was able to refold the substrate significantly (~10%). It should be noted that thioredoxin, which is a reductase that resides in the cytoplasm of bacteria, was unable to refold the substrate regardless of its redox state, while DsbA, an oxidase in the bacterial periplasm, showed weak but still significant activity under the same conditions, indicating the validity of this assay system. In addition to the Fab refolding assay, a scrambled RNase assay was performed. In this assay, RNase A was reduced and then re-oxidized to form non-native disulfide bonds, thereby testing isomerase activity by monitoring RNase A activity. The results showed patterns similar to the Fab refolding assay, i.e., ERp23 activated the scrambled RNase A significantly compared to the control, while the activity detected was about half of the PDI. Together, these two in vitro studies indicated that recombinant ERp23 protein possessed oxidoreductase activity.

Since disulfide bonds are formed via a transfer reaction that involves an intermediate step where the catalytic enzyme forms a mixed disulfide with the substrate (Sevier & Kaiser (2002) *Nat. Rev. Mol. Cell. Biol.* 3:836-47), it was determined whether ERp23 formed a covalent disulfide bond with IgM assembly intermediates in plasma cells. Purified mouse splenic B cells were treated with LPS, and the resulting plasma cells were metabolically labeled with $^{35}$S-Met/Cys.

Subsequently, the cells were lysed under acidic conditions, to prevent post-lysis disulfide exchange, and in the presence of N-ethyl maleimide (NEM), to block free thiols. ERp23 was immunoprecipitated with a rabbit polyclonal anti-ERp23 antibody (non-immune rabbit IgG was used as a negative control), and the precipitated proteins were separated by SDS-PAGE. Under non-reducing conditions, free ERp23, as well as several slower migrating proteins, were precipitated specifically with the anti-ERp23 antiserum. Of note, ERp23 migrated slower under reducing conditions, indicating that ERp23 possessed at least one intra-chain disulfide bond. When the sample was separated under reducing conditions, all of the slower migrating bands observed under non-reducing conditions resolved into two predominant bands migrating at ~75 kDa and 25 kDa, which are the same size as IgM heavy chain (HC) and light chain (LC), respectively. In order to directly show that ERp23 formed mixed disulfide with the co-precipitated proteins, the same sample was subjected to two-dimensional SDS-PAGE, in which the first dimension was separated under non-reducing conditions and the second under reducing conditions. Using this method, two spots containing ERp23 were detected; the major spot was near the diagonal, which represents free ERp23, and the second minor spot, which migrated slower during the first dimension. The fact that this second ERp23 spot was directly below two other spots (75 and 25 kDa) indicated that ERp23 formed a mixed disulfide with these proteins, which were identified as IgM HC and LC by western blot analysis. These data further indicated that ERp23 was an oxidoreductase, and clearly demonstrated that immunoglobulins are a natural substrate of ERp23.

It was noted that ERp23 only formed mixed disulfides with IgM monomers ($H_2L_2$), which form disulfide bonds with J chain to assemble into pentamers ($H_2L_2)_5$, but it was not covalently associated with free H, HL intermediates or higher order $H_2L_2$ oligomers, which were also co-precipitated. This indicated that although ERp23 can interact with all the IgM assembly intermediates non-covalently, it appeared to only be required for oxidizing/reducing specific disulfide bonds in the Igs or that some disulfides were more rate limiting than others in IgM assembly (e.g., those involved in pentamerization).

To further confirm the oxidoreductase activity of ERp23, stable cell lines with decreased ERp23 expression were generated. This was achieved by expressing ERp23-specific shRNA in the Ag8(8) plasmacytoma cell line ($\gamma^+$, $\kappa^-$) where ERp23 was first identified. Two different RNA sequences were targeted and two independent single-cell clones were isolated for each sequence. Western blot analysis confirmed that ERp23 levels were significantly reduced in all four clones, while the steady state levels of γHC were not detectably changed. The folding and assembly of γHC in pulse-chase experiments was analyzed in a vector control line and in the knock-down clones. Cells were metabolically labeled with $^{35}$S-Met/Cys for 5 minutes and then chased for the indicated times. Cells were lysed in NP-40 containing buffer including NEM, and γHCs were precipitated with protein-A beads and separated by SDS-PAGE run under both non-reducing and reducing conditions. In the vector control line, the γHC monomer ($H_1$) was detected initially, but within 10 minutes it assembled into a dimeric form ($H_2$). A second band was present in the region of the gel where HC was expected to migrate, and a band at the predicted size of BiP was also detected. When ERp23 expression was significantly diminished, the assembly of HC monomers to dimers appeared to be unaffected. However, in all four clones, two consistent differences were observed. First, there was only a single band present where HC monomers should migrate, and second, high molecular weight complexes were found near the top of the gel at later time points. Analysis of the same immunoprecipitated material under reducing conditions revealed only two bands in both vector control and ERp23 knock down clones; one that represented γHC and one that represented BiP. This indicated that the HC doublet observed at early time points in the vector control line likely represented two different oxidation intermediates of the HC and that the very slow migrating bands were disulfide bonded HC aggregates, indicating that HC stability was also affected. To demonstrate this, another pulse-chase experiment was carried out, this time with a longer pulse (20 minutes) and chase period (i.e., 8, 24, and 48 hours). While the level of radiolabeled γHC in control cells stayed ~100% during the first 8 hours before starting to degrade, γHC in all of the knock down lines started degrading immediately without the 8 hour lag, which likely represents the folding phase. Thus, degradation of unassembled γHC appeared to be much faster in the absence of ERp23.

It has been shown that the $C_H1$ domain of incompletely assembled HC, which is the site of covalent attachment of LC, remains unoxidized in non-lymphoid cell lines (Lee, et al. (1999) *Mol. Biol. Cell* 10:2209-19). To determine whether differences in the oxidation of the $C_H1$ domain were responsible for the altered HC mobility observed in the ERp23 knockdown cells, the oxidation of the $C_H1$ domain was examined in the presence and absence of ERp23 using a simplified mini HC possessing only a $V_H$ and $C_H1$ domain ($V_H$-$C_H1$) (Lee, et al. (1999) supra). When this mini HC was expressed in 293T cells alone, the $V_H$ domain was oxidized, but the $C_H1$ domain remained reduced. As expected, when LC was co-expressed, the $C_H1$ domain was oxidized in the HC that assembled with LC. Surprisingly, co-expression of wild-type human ERp23 resulted in oxidation of the $C_H1$ domain in a portion of the HC even in the absence of LC. Given that ERp23 is expressed in lymphoid cells including the Ag8(8) cell line, this result indicates that the two forms of γHC observed at early time points in the vector control cells represent two different redox states for the HC.

By using this system to monitor ERp23 activity, a series of cysteine mutants (Cys→Ser) were produced for human ERp23. These proteins were co-expressed with the mini HC construct to determine which residues among the six conserved cysteines (Cys50, Cys53, Cys95, Cys143, Cys171, and Cys178, with reference to human ERp23, FIG. 1) were important for the oxidoreductase activity. First, the activity of each of the six different single cysteine mutants was tested and like wild-type ERp23, which fully oxidizes ~24% of the mini HC, the Cys50Ser mutant showed a similar ability to oxidize the $C_H1$ domain (i.e., 20%). This was unexpected since Cys50 is the first cysteine in the Cys-Xaa-Yaa-Cys (SEQ ID NO:4) motif that is expected to be the active site. The Cys178Ser mutant also showed some activity, although it was slightly weaker than that observed with wild-type ERp23 or the Cys50Ser mutant. All of the remaining single cysteine mutants had significantly reduced activity, which in most cases was similar to that observed when no ERp23 was co-expressed.

To determine the presence and/or location of disulfide bonds, ERp23 protein was overexpressed in 293T cells as an HA-tagged protein, isolated, treated with trypsin, and subjected to mass spectrophometric analysis. This analysis indicated that Cys95 and Cys143 formed a disulfide bond, as well as either Cys50-Cys178 and Cys53-Cys171 or Cys50-Cys171 and Cys53-Cys178; trypsin digestion could not distinguish between these possibilities. Subsequently, pair-wise mutations were produced based on the predicted disulfide bond pattern. When these double mutants were examined, it was observed that only the Cys50-178Ser mutant still retained activity. This is in keeping with the observation that mutation of either Cys50Ser or Cys178Ser did not completely destroy oxidase activity. Moreover, this demonstrates that this pair is disposable for activity in vivo. On the other hand, two other double mutants did not show activity. Since earlier data revealed that ERp23 possessed at least one far ranging disulfide bond based on differences in mobility after reduction, it should be noted that loss of activity could be due to either mutation of the active site or to dramatic conformational changes in the protein that secondarily affect activity.

Another method of identifying active site cysteines in PDI-like proteins that have isomerase/reductase activity has been to mutate one or the other of the two cysteines in the Cys-Xaa-Yaa-Cys (SEQ ID NO:4) motif (Walker & Gilbert (1997) *J. Biol. Chem.* 272:8845-8; Walker, et al. (1996) *Biochemistry* 35:1972-80). Such mutation can result in the formation of more stable mixed disulfide bonds with the substrate, since the free cysteine can now attack an existing disulfide bonds in the substrate, but is unable to resolve the situation by accepting the disulfide bond. Thus, a number of the single cysteine mutants disclosed herein were tested for their ability to form stable mixed disulfide bonds with the mini HC. After lysing the cells with lysis buffer in the presence of NEM, HA-tagged mini HC ($V_H$-$C_H1$) was immunoprecipitated with the anti-HA monoclonal antibody, subjected to two-dimensional SDS-PAGE, and analyzed by western blot using both anti-HA and anti-ERp23 antibodies. Only one ERp23 spot appeared along the diagonal when the HC were immunoprecipitated from cells co-expressing wild-type ERp23 or the no cysteine mutant (negative control). This indicates that a small amount of ERp23 binds non-covalently to the mini HC, even when it possesses no intramolecular disulfide bonds. The two spots observed on the far right side of the blot represent the HC and LC of the precipitating antibody. Mixed disulfides were not detected between either the Cys50Ser or Cys53Ser mutant and the mini HC, even though trace amounts of ERp23 did bind to the HC in both cases. It was observed that all of the single cysteine mutants appeared at the bottom right of the gel. This is likely because more mutants were observed in the BiP-HC complex without any treatment. However, when the Cys95Ser and Cys178Ser mutants (and to a lesser extent the Cys143Ser mutant) were examined, it was found that immunoprecipitation of the mini HC resulted in the co-precipitation of disulfide linked ERp23. In fact, in all three cases, two species of HC complexed with ERp23 were detected. This likely represents an ERp23 bound to two cysteines, or perhaps more likely, that the larger molecular form represents ERp23 dimers bound to one free cysteine that was originally part of a disulfide bond.

At least 19 PDI family members have been identified in humans. These proteins all form a thioredoxin like fold that contains the Cys-Xaa-Xaa-Cys (SEQ ID NO:11) active site (Appenzeller-Herzog, et al. (2008) *Biochim. Biophys. Acta* 1783:535-48; Ellgaard & Ruddock (2005) supra). In addition, yeast and mammals possess flavoproteins (Ero1 and Erv2) that serve to oxidize PDI family members. These proteins are largely α helical, and therefore do not form a thioredoxin fold, but nonetheless transfer disulfide bonds through the same Cys-Xaa-Xaa-Cys (SEQ ID NO:11) motif (Sevier & Kaiser (2002) supra). Although ERp23 has the Cys-Xaa-Xaa-Cys (SEQ ID NO:11) motif, the analysis herein revealed that the amino-terminal cysteine residue (Cys50) is not necessary for the activity, indicating that the Cys-Xaa-Xaa-Cys (SEQ ID NO:11) motif of ERp23 is less likely to be the active site. On the other hand, the analyses herein raised the possibility of Cys95 and Cys143 as active cysteines, which are surprisingly located far apart from each other. Thus, together with a prediction of highly alpha-helical structure, ERp23 appears to be a non-conventional oxidoreductase. In addition, since the characteristics of the ERp23 are completely different from the known oxidoreductases, it is likely that there are other proteins that can catalyze disulfide metabolism through cysteines that does not form the Cys-Xaa-Xaa-Cys (SEQ ID NO:11) motif.

Among the known oxidoreductases, most of them are ubiquitously expressed in all tissues, and there are only a few examples that have limited expression pattern, such as PDIp, PDILT and ERp46 (Ellgaard & Ruddock (2005) supra). While it seems that the reason for an organism to have tissue-specific oxidoreductases is to deal with its specific substrates, none of them have been identified to have its own client. This is likely due to the difficulty in detecting the mixed disulfide intermediate between the enzyme and the substrate, since transferring disulfides are transient (Appenzeller-Herzog, et al. (2008) supra). In fact, even including other oxidoreductases, only two examples have been known to form mixed disulfides between endogenous proteins; PDI and MHC class I heavy chain in HeLa cells (Park, et al. (2006) *Cell* 127:369-82), and PDI and ERp57 with thyroglobulin (Di Jeso, et al. (2005) *Mol. Cell. Biol.* 25:9793-805). Thus, it is very unique that ERp23 is expressed only in lymphoid tissues, and that the mixed disulfide were detectable between both endogenous ERp23 and IgM, strongly indicating that at least IgM and likely other types of Igs are the natural substrate of the ERp23.

What is claimed is:

1. A method for enhancing recombinant antibody production comprising recombinantly co-expressing in a host cell a recombinant antibody and the endoplasmic reticulum oxidoreductase protein of SEQ ID NO:1 or SEQ ID NO:2 thereby enhancing production of the recombinant antibody.

* * * * *

SEQUENCE LISTING

<160> NUMBER OF SEQ ID NOS: 11

<210> SEQ ID NO 1
<211> LENGTH: 188
<212> TYPE: PRT
<213> ORGANISM: Mus musculus

<400> SEQUENCE: 1

Met Arg Leu Pro Leu Pro Leu Leu Leu Leu Gly Cys Arg Ala Ile
1               5                   10                  15

Leu Gly Ser Ala Gly Asp Arg Val Ser Leu Ser Ala Ser Ala His Thr
            20                  25                  30

-continued

Leu Asp Asp Glu Glu Lys Tyr Ser Ala His Met Pro Ala His Leu Arg
         35                  40                  45

Cys Asp Ala Cys Arg Ala Val Ala Phe Gln Met Gly Gln Arg Leu Ala
 50                  55                  60

Lys Ala Glu Ala Lys Ser His Thr Pro Asp Ala Ser Gly Leu Gln Glu
 65                  70                  75                  80

Leu Ser Glu Ser Thr Tyr Thr Asp Val Leu Asp Gln Thr Cys Ser Gln
                 85                  90                  95

Asn Trp Gln Ser Tyr Gly Val His Glu Val Asn Gln Met Lys Arg Leu
                100                 105                 110

Thr Gly Pro Gly Leu Ser Lys Gly Pro Glu Pro Arg Ile Ser Val Met
            115                 120                 125

Ile Ser Gly Gly Pro Trp Pro Asn Arg Leu Ser Lys Thr Cys Phe His
        130                 135                 140

Tyr Leu Gly Glu Phe Gly Glu Asp Gln Ile Tyr Glu Ala Tyr Arg Gln
145                 150                 155                 160

Gly Gln Ala Asn Leu Glu Ala Leu Leu Cys Gly Gly Thr His Gly Pro
                165                 170                 175

Cys Ser Gln Glu Ile Leu Ala Gln Arg Glu Glu Leu
            180                 185

<210> SEQ ID NO 2
<211> LENGTH: 189
<212> TYPE: PRT
<213> ORGANISM: Homo sapiens

<400> SEQUENCE: 2

Met Arg Leu Ser Leu Pro Leu Leu Leu Leu Leu Gly Ala Trp Ala
1               5                   10                  15

Ile Pro Gly Gly Leu Gly Asp Arg Ala Pro Leu Thr Ala Thr Ala Pro
             20                  25                  30

Gln Leu Asp Asp Glu Met Tyr Ser Ala His Met Pro Ala His Leu
         35                  40                  45

Arg Cys Asp Ala Cys Arg Ala Val Ala Tyr Gln Met Trp Gln Asn Leu
 50                  55                  60

Ala Lys Ala Glu Thr Lys Leu His Thr Ser Asn Ser Gly Gly Arg Arg
 65                  70                  75                  80

Glu Leu Ser Glu Leu Val Tyr Thr Asp Val Leu Asp Arg Ser Cys Ser
                 85                  90                  95

Arg Asn Trp Gln Asp Tyr Gly Val Arg Glu Val Asp Gln Val Lys Arg
                100                 105                 110

Leu Thr Gly Pro Gly Leu Ser Glu Gly Pro Glu Pro Ser Ile Ser Val
            115                 120                 125

Met Val Thr Gly Gly Pro Trp Pro Thr Arg Leu Ser Arg Thr Cys Leu
        130                 135                 140

His Tyr Leu Gly Glu Phe Gly Glu Asp Gln Ile Tyr Glu Ala His Gln
145                 150                 155                 160

Gln Gly Arg Gly Ala Leu Glu Ala Leu Leu Cys Gly Pro Gln Gly
                165                 170                 175

Ala Cys Ser Glu Lys Val Ser Ala Thr Arg Glu Glu Leu
            180                 185

<210> SEQ ID NO 3
<211> LENGTH: 189
<212> TYPE: PRT
<213> ORGANISM: Artificial Sequence
<220> FEATURE:

-continued

```
<223> OTHER INFORMATION: Synthetic polypeptide
<220> FEATURE:
<221> NAME/KEY: MISC_FEATURE
<222> LOCATION: (4)..(4)
<223> OTHER INFORMATION: Xaa denotes Pro or Ser
<220> FEATURE:
<221> NAME/KEY: MISC_FEATURE
<222> LOCATION: (5)..(5)
<223> OTHER INFORMATION: Xaa denotes Leu
<220> FEATURE:
<221> NAME/KEY: MISC_FEATURE
<222> LOCATION: (7)..(7)
<223> OTHER INFORMATION: Xaa denotes Leu or is absent
<220> FEATURE:
<221> NAME/KEY: MISC_FEATURE
<222> LOCATION: (14)..(14)
<223> OTHER INFORMATION: Xaa denotes Cys or Ala
<220> FEATURE:
<221> NAME/KEY: MISC_FEATURE
<222> LOCATION: (15)..(15)
<223> OTHER INFORMATION: Xaa denotes Arg or Trp
<220> FEATURE:
<221> NAME/KEY: MISC_FEATURE
<222> LOCATION: (18)..(18)
<223> OTHER INFORMATION: Xaa denotes Leu or Pro
<220> FEATURE:
<221> NAME/KEY: MISC_FEATURE
<222> LOCATION: (20)..(20)
<223> OTHER INFORMATION: Xaa denotes Ser or Gly
<220> FEATURE:
<221> NAME/KEY: MISC_FEATURE
<222> LOCATION: (21)..(21)
<223> OTHER INFORMATION: Xaa denotes Ala or Leu
<220> FEATURE:
<221> NAME/KEY: MISC_FEATURE
<222> LOCATION: (25)..(25)
<223> OTHER INFORMATION: Xaa denotes Val or Ala
<220> FEATURE:
<221> NAME/KEY: MISC_FEATURE
<222> LOCATION: (26)..(26)
<223> OTHER INFORMATION: Xaa denotes Ser or Pro
<220> FEATURE:
<221> NAME/KEY: MISC_FEATURE
<222> LOCATION: (32)..(32)
<223> OTHER INFORMATION: Xaa denotes His or Pro
<220> FEATURE:
<221> NAME/KEY: MISC_FEATURE
<222> LOCATION: (33)..(33)
<223> OTHER INFORMATION: Xaa denotes Thr or Gln
<220> FEATURE:
<221> NAME/KEY: MISC_FEATURE
<222> LOCATION: (39)..(39)
<223> OTHER INFORMATION: Xaa denotes Lys or Met
<220> FEATURE:
<221> NAME/KEY: MISC_FEATURE
<222> LOCATION: (61)..(61)
<223> OTHER INFORMATION: Xaa denotes Gly or Trp
<220> FEATURE:
<221> NAME/KEY: MISC_FEATURE
<222> LOCATION: (63)..(63)
<223> OTHER INFORMATION: Xaa denotes Arg or Asn
<220> FEATURE:
<221> NAME/KEY: MISC_FEATURE
<222> LOCATION: (69)..(69)
<223> OTHER INFORMATION: Xaa denotes Ala or Thr
<220> FEATURE:
<221> NAME/KEY: MISC_FEATURE
<222> LOCATION: (71)..(71)
<223> OTHER INFORMATION: Xaa denotes Ser or Leu
<220> FEATURE:
<221> NAME/KEY: MISC_FEATURE
<222> LOCATION: (74)..(74)
<223> OTHER INFORMATION: Xaa denotes Pro or Ser
<220> FEATURE:
<221> NAME/KEY: MISC_FEATURE
<222> LOCATION: (75)..(75)
<223> OTHER INFORMATION: Xaa denotes Asp or Asn
<220> FEATURE:
<221> NAME/KEY: MISC_FEATURE
<222> LOCATION: (77)..(77)
```

-continued

```
<223> OTHER INFORMATION: Xaa denotes Ser or Gly
<220> FEATURE:
<221> NAME/KEY: MISC_FEATURE
<222> LOCATION: (79)..(79)
<223> OTHER INFORMATION: Xaa denotes Leu or Arg
<220> FEATURE:
<221> NAME/KEY: MISC_FEATURE
<222> LOCATION: (80)..(80)
<223> OTHER INFORMATION: Xaa denotes Gln or Arg
<220> FEATURE:
<221> NAME/KEY: MISC_FEATURE
<222> LOCATION: (85)..(85)
<223> OTHER INFORMATION: Xaa denotes Ser or Leu
<220> FEATURE:
<221> NAME/KEY: MISC_FEATURE
<222> LOCATION: (86)..(86)
<223> OTHER INFORMATION: Xaa denotes Thr or Val
<220> FEATURE:
<221> NAME/KEY: MISC_FEATURE
<222> LOCATION: (93)..(93)
<223> OTHER INFORMATION: Xaa denotes Gln or Arg
<220> FEATURE:
<221> NAME/KEY: MISC_FEATURE
<222> LOCATION: (97)..(97)
<223> OTHER INFORMATION: Xaa denotes Gln or Arg
<220> FEATURE:
<221> NAME/KEY: MISC_FEATURE
<222> LOCATION: (101)..(101)
<223> OTHER INFORMATION: Xaa denotes Ser or Asp
<220> FEATURE:
<221> NAME/KEY: MISC_FEATURE
<222> LOCATION: (105)..(105)
<223> OTHER INFORMATION: Xaa denotes His or Arg
<220> FEATURE:
<221> NAME/KEY: MISC_FEATURE
<222> LOCATION: (108)..(108)
<223> OTHER INFORMATION: Xaa denotes Asn or Asp
<220> FEATURE:
<221> NAME/KEY: MISC_FEATURE
<222> LOCATION: (120)..(120)
<223> OTHER INFORMATION: Xaa denotes Lys or Glu
<220> FEATURE:
<221> NAME/KEY: MISC_FEATURE
<222> LOCATION: (125)..(125)
<223> OTHER INFORMATION: Xaa denotes Arg or Ser
<220> FEATURE:
<221> NAME/KEY: MISC_FEATURE
<222> LOCATION: (137)..(137)
<223> OTHER INFORMATION: Xaa denotes Asn or Thr
<220> FEATURE:
<221> NAME/KEY: MISC_FEATURE
<222> LOCATION: (144)..(144)
<223> OTHER INFORMATION: Xaa denotes Phe or Leu
<220> FEATURE:
<221> NAME/KEY: MISC_FEATURE
<222> LOCATION: (160)..(160)
<223> OTHER INFORMATION: Xaa denotes Arg or Gln
<220> FEATURE:
<221> NAME/KEY: MISC_FEATURE
<222> LOCATION: (163)..(163)
<223> OTHER INFORMATION: Xaa denotes Arg or Gln
<220> FEATURE:
<221> NAME/KEY: MISC_FEATURE
<222> LOCATION: (165)..(165)
<223> OTHER INFORMATION: Xaa denotes Asn or Ala
<220> FEATURE:
<221> NAME/KEY: MISC_FEATURE
<222> LOCATION: (174)..(174)
<223> OTHER INFORMATION: Xaa denotes Thr or Pro
<220> FEATURE:
<221> NAME/KEY: MISC_FEATURE
<222> LOCATION: (175)..(175)
<223> OTHER INFORMATION: Xaa denotes His or Gln
<220> FEATURE:
<221> NAME/KEY: MISC_FEATURE
<222> LOCATION: (177)..(177)
<223> OTHER INFORMATION: Xaa denotes Pro or Ala
<220> FEATURE:
<221> NAME/KEY: MISC_FEATURE
<222> LOCATION: (180)..(180)
```

```
<223> OTHER INFORMATION: Xaa denotes Glu or Gln
<220> FEATURE:
<221> NAME/KEY: MISC_FEATURE
<222> LOCATION: (181)..(181)
<223> OTHER INFORMATION: Xaa denotes Glu or Lys
<220> FEATURE:
<221> NAME/KEY: MISC_FEATURE
<222> LOCATION: (183)..(183)
<223> OTHER INFORMATION: Xaa denotes Leu or Ser
<220> FEATURE:
<221> NAME/KEY: MISC_FEATURE
<222> LOCATION: (185)..(185)
<223> OTHER INFORMATION: Xaa denotes Gln or Thr

<400> SEQUENCE: 3

Met Arg Leu Xaa Xaa Pro Xaa Leu Leu Leu Leu Gly Xaa Xaa Ala
 1               5                  10                  15

Ile Xaa Gly Xaa Xaa Gly Asp Arg Xaa Xaa Leu Ser Ala Ser Ala Xaa
         20                  25                  30

Xaa Leu Asp Asp Glu Glu Xaa Tyr Ser Ala His Met Pro Ala His Leu
             35                  40                  45

Arg Cys Asp Ala Cys Arg Ala Val Ala Phe Gln Met Xaa Gln Xaa Leu
 50                  55                  60

Ala Lys Ala Glu Xaa Lys Xaa His Thr Xaa Xaa Ala Xaa Gly Xaa Xaa
 65                  70                  75                  80

Glu Leu Ser Glu Xaa Xaa Tyr Thr Asp Val Leu Asp Xaa Ser Cys Ser
                 85                  90                  95

Xaa Asn Trp Gln Xaa Tyr Gly Val Xaa Glu Val Xaa Gln Met Lys Arg
                100                 105                 110

Leu Thr Gly Pro Gly Leu Ser Xaa Gly Pro Glu Pro Xaa Ile Ser Val
            115                 120                 125

Met Ile Ser Gly Gly Pro Trp Pro Xaa Arg Leu Ser Lys Thr Cys Xaa
        130                 135                 140

His Tyr Leu Gly Glu Phe Gly Glu Asp Gln Ile Tyr Glu Ala His Xaa
145                 150                 155                 160

Gln Gly Xaa Ala Xaa Leu Glu Ala Leu Leu Cys Gly Xaa Xaa Gly
                165                 170                 175

Xaa Cys Ser Xaa Xaa Ile Xaa Ala Xaa Arg Glu Glu Leu
            180                 185

<210> SEQ ID NO 4
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa denotes Asp
<220> FEATURE:
<221> NAME/KEY: MISC_FEATURE
<222> LOCATION: (3)..(3)
<223> OTHER INFORMATION: Xaa denotes Ala

<400> SEQUENCE: 4

Cys Xaa Xaa Cys
 1

<210> SEQ ID NO 5
<211> LENGTH: 25
<212> TYPE: DNA
<213> ORGANISM: Artificial Sequence
```

-continued

```
<220> FEATURE:
<223> OTHER INFORMATION: Synthetic oligonucleotide

<400> SEQUENCE: 5
ctacacttgc tgaactggct cctgg                                           25

<210> SEQ ID NO 6
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 6
ggagggtaga gtccaggact agagctc                                         27

<210> SEQ ID NO 7
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 7
gccatgagac tgcctctgcc ac                                              22

<210> SEQ ID NO 8
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 8
aagctcttct ctctgggcca gg                                              22

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9
ctcagtacga gaggaaccgc                                                 20

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10
cggattctga cttagaggcg                                                 20

<210> SEQ ID NO 11
<211> LENGTH: 4
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: misc_feature
<222> LOCATION: (2)..(3)
<223> OTHER INFORMATION: Xaa can be any naturally occurring amino acid

<400> SEQUENCE: 11

Cys Xaa Xaa Cys
1
```